United States Patent
de Sternberg Stojalowski

(10) Patent No.: US 11,957,809 B2
(45) Date of Patent: Apr. 16, 2024

(54) PROCESS CHALLENGE DEVICE FOR EVALUATION OF CONTAMINATION FORMING AND REMOVAL PROCESSES INSIDE OF HOLLOW CHANNELS AND METHODS FOR CONTAMINATION EVALUATION

(71) Applicant: ASEPTIUM LIMITED, Bishop's Stortford (GB)

(72) Inventor: Pawel de Sternberg Stojalowski, Bishop's Stortford (GB)

(73) Assignee: ASEPTIUM LIMITED, Bishop's Stortford (GB)

( * ) Notice: Subject to any disclaimer, the term of this patent is extended or adjusted under 35 U.S.C. 154(b) by 507 days.

(21) Appl. No.: 16/864,034

(22) Filed: Apr. 30, 2020

(65) Prior Publication Data
US 2020/0254127 A1 Aug. 13, 2020

Related U.S. Application Data

(63) Continuation of application No. PCT/PL2018/050056, filed on Oct. 30, 2018.

(30) Foreign Application Priority Data

Oct. 31, 2017 (GB) ...................................... 1718005

(51) Int. Cl.
*A61L 2/28* (2006.01)
*A61L 2/18* (2006.01)
*A61L 2/24* (2006.01)

(52) U.S. Cl.
CPC .................. *A61L 2/28* (2013.01); *A61L 2/18* (2013.01); *A61L 2/24* (2013.01);
(Continued)

(58) Field of Classification Search
CPC ..... A61L 2/28; A61L 2/18; A61L 2/24; A61L 2202/121; A61L 2202/122; A61L 2202/15;
(Continued)

(56) References Cited

U.S. PATENT DOCUMENTS

| 2008/0003689 A1* | 1/2008 | Lee ................... G01N 30/0005 436/174 |
| 2011/0182770 A1* | 7/2011 | Chandrapati ............ C12Q 1/22 422/292 |

(Continued)

*Primary Examiner* — Regina M Yoo
(74) *Attorney, Agent, or Firm* — Andrzej Malarz, Esq.

(57) ABSTRACT

A process challenge device for evaluation of contamination forming and removal processes inside of narrow and hollow channels comprising sample of at one sample, at least capsule having an inlet connector, a flow shaping element and an internal cavity for holding said sample, a lock—or end cap—for each capsule securing the sample inside the cavity characterized by said tag located in the capsule against one of the walls of the internal cavity that is shaped not to change the parameters of the fluid flow while it flows into said cavity and over the face of the sample simulating the flow through an equivalent narrow channel.

Methods for evaluation of contamination forming and removal processes inside of narrow and hollow channels with said process challenge device having removable and replaceable samples characterised by said process challenge device being loaded with a matching sample containing contamination for evaluation of effectiveness of a cleaning processes or blank sample for evaluation of contamination formation processes on said sample.

12 Claims, 1 Drawing Sheet

(52) U.S. Cl.
CPC ... *A61L 2202/121* (2013.01); *A61L 2202/122* (2013.01); *A61L 2202/15* (2013.01); *A61L 2202/17* (2013.01); *A61L 2202/182* (2013.01); *A61L 2202/24* (2013.01)

(58) Field of Classification Search
CPC .......... A61L 2202/17; A61L 2202/182; A61L 2202/24; B01L 2300/0609; B01L 2300/0838; B01L 3/5027; C12Q 1/22
See application file for complete search history.

(56) References Cited

U.S. PATENT DOCUMENTS

2013/0210069 A1\* 8/2013 Pederson .................. A61L 2/28
435/288.7
2018/0360493 A1\* 12/2018 Baker ................ A61B 5/14503

\* cited by examiner

PROCESS CHALLENGE DEVICE FOR EVALUATION OF CONTAMINATION FORMING AND REMOVAL PROCESSES INSIDE OF HOLLOW CHANNELS AND METHODS FOR CONTAMINATION EVALUATION

CROSS REFERENCE TO RELATED APPLICATIONS

This application is a continuation under 35 U.S.C. § 120 of International Application PCT/PL2018/050056, filed Oct. 30, 2018, which claims priority to Great Britain Application 1718005.0, filed Oct. 31, 2017, the contents of each of which are incorporated by reference herewith.

FIELD OF INVENTION

This disclosure relates to the life sciences and decontamination sciences, and more particularly to process challenge device, hereafter known as PCDs for evaluation of biological and chemical contamination formation on internal surfaces or walls of tubes, pipes, lumens or channels as well as effectiveness of removal of biological and chemical contamination from the insides of aforementioned internal surfaces. Said PCDs simulate medical and laboratory instruments and equipment or elements of said instruments and equipment used in health care, including medicine and dentistry, morgues and veterinary settings, as well as life sciences research and development, where such instruments and equipment are contaminated or potentially contaminated with biological or chemical materials.

BACKGROUND

Process challenge device for evaluation of decontamination processes such as ones presented in patents WO2016164329, U.S. Pat. No. 6,653,096, WO2016009204 and DE 10 2013 000 161 are commonly known in the industry. Contamination on internal surfaces of tubes, pipes, lumens and channels, hereafter collectively known as channels may be of biological and chemical nature.

Biological contamination may come in the form of biofilms, which are thin layers of microorganisms adhering to the surfaces and are commonly found on medical and laboratory equipment, especially inside of channels. Biofilms grow and can be grown on surfaces by exposing them to the conditions enabling microbial growth. Typically, to grow biofilm on the inside of channels below 20 mm in diameter, similar to ones used inside of flexible endoscopes, internal walls of the said channel would be exposed to a fluid containing microbial flora for a period of time in a controlled environment. Once a biofilm is grown in such conditions, it must be extracted or removed from those channels for the purpose of further research. Processes of biofilm extraction from narrow channels are laborious, problematic and typically involve cutting the channel into samples and irreversibly damaging the tube.

Chemical contamination inside channels, similarly to biological contamination, is formed through exposure of surfaces to contaminants typically suspended or diluted in fluids that internal surfaces get exposed to. Often a combination of biological and chemical contamination is found where chemical contamination becomes a structure to which biological contamination adheres and is built on.

In both cases, a greater understanding of the aforementioned processes is required to gain the ability to form and remove contamination from internal surfaces of narrow channels effectively. PCDs are often used in place of actual instruments where it is impossible to test said instruments without damaging or disassembling them or when it is impractical or not cost-effective to do so. Beyond that, PCDs offer repeatability of test conditions that allow for statistical analysis of results.

Decontamination sciences explore ways of removing contamination from surfaces (cleaning) and inactivating (killing) it through disinfection and/or sterilisation. Biological and chemical contaminations are a major problem for instruments and equipment with narrow channels like flexible and rigid endoscopes which are routinely used in medicine, hand-pieces in dentistry and ophthalmology, or polymer tubing in research and development and scientific research. Typically, a cleaning process of channels involves flushing and soaking them in cleaning detergent, sometimes manual brushing and removal through abrasion, automated cleaning in washers or washer disinfectors that involve internal flushing under pressure and sometimes ultrasonication. Disinfection and sterilisation are achieved by exposing surfaces to disinfecting or sterilising agents (temperatures above 70° C., chemicals, gases, irradiation). Conventional PCDs that are used to evaluate cleaning performance typically consist of coupons or samples inoculated with biological or chemical test substance. Such prepared samples undergo cleaning processes in question and are evaluated after for detection of any remaining contamination.

Evaluation of the internal cleaning of instrumentation with channels is particularly difficult since PCDs must realistically simulate conditions occurring on the internal surfaces of narrow channels during the washing process. Typically, rectangular samples, hereafter known as tags, are made out of surgical stainless steel 316L and are 2 mm to 20 mm wide and 20 mm to 120 mm long, contaminated with various amounts of test soil which can be of biological, chemical or mixed nature. Such prepared samples are placed inside cylindrical capsules with one or both ends connected to the narrow channels (1 mm to 20 mm internal diameter) such that fluid pumped into the channels flows through the capsule and washes away contamination from the tag contained within. Such constructed process challenge devices create unrealistic cleaning conditions inside of the capsule. The internal flow parameters inside the capsule are often very different from the narrow tubes that they are designed to scrutinise. They are characterised by much lower fluid velocity inside the capsule and unwanted turbulence resulting from significantly changing the internal geometry (a large increase of internal diameter when fluid enters the capsule and/or sudden change of shape especially if the change of shape creates edges perpendicular to the direction of the flow). Additionally, because typically the tag is positioned in the middle of the cylindrical capsule where the flow velocity is highest, it also splits the flow into two streams on each side of the tag creating considerably different conditions from those found at the walls of a narrow channel.

In those cases where capsule cavities are designed to hold tags on one side of the cavity such that the flow flows around one side of the tag only as described in DE 10 2013 000 161 there is a risk of operators inserting tags wrong way round and producing false results.

The aforementioned types of PCDs are typically used in sterile services facilities in hospitals, as well as in research and development laboratories, morgues and veterinary practices. Whether it is in the case of simulating biofilm growth on narrow lumen walls or internal cleaning replication of realistic conditions is critical to the concept of PCDs. Making more realistic challenges will lead to a more in-depth understanding of contamination formation processes and improve cleaning performance evaluation techniques that in turn will reduce the risk of healthcare-acquired infections linked to medical equipment with narrow channels and lumens.

SUMMARY

The present invention relates to PCDs for biofilm growth and internal cleaning evaluation characterised with optimised internal geometries realistically simulating the inside of narrow channels, means to prevent positioning the tag inside the capsule wrong way round and allowing for convenient and non-destructive evaluation of results.

The present invention provides a PCD, containing a hollow capsule having an inlet and outlet, with at least one removable test tag positioned inside said capsules cavity, containing a flow shaping part and tag holding part containing means to position the tag in a correct orientation, and optionally one or more channels connected to the inlet and or the outlet of the capsule such that internal volume of the channels and capsule cavity create one continuous volume so fluid can flow through it without a loss.

According to a preferred embodiment of the present invention, the aforementioned tag is a piece of solid material that contamination is intended to form or be removed from. Said tag is defined by its length being at least twice as long as the width and least five times longer than its depth. The tag can either be symmetrical or asymmetrical against at least one the plane drawn alongside its length. The face of the tag is perpendicular to the direction defining its depth. The face of the tag is used as the working surface that contamination is formed on, applied to and removed from.

According to a preferred embodiment of the present invention, the aforementioned capsule contains a longitudinal internal cavity containing a flow shaping part and tag holding the part. Flow shaping part gradually changes the shape of the flow from the inlet shape into the shape of the cavity that holds the tag. Tag holding part contains a seat that holds a removable tag and allows for the stream of fluid to flow over one of the faces of the tag. Said internal cavity's cross-section area, perpendicular to the direction of the fluid flow, excluding cross-section area of the tag, is between 95% and 105% of the matching internal cross-section area (not necessarily circular) of the hollow channel it is intended to simulate. Said cavity's cross-section size does not change by more than 10% per every 10% of its length along the first 80% of the length of the capsule, measured from the inlet side. This allows for the fluid flowing from the capsule's inlet through the flow shaping part into the tag holding part of the cavity not to change velocity by more than 10%, and/or direction by more than a 5° angle from the direction at the inlet to the capsule's cavity. In accordance with a preferred embodiment of the present invention, the tag holding part of the cavity of the capsule is shaped such that it forms matching seat for the tag such that the tag is positioned internally against one side of said cavity in order for the fluid to flow only over one side of the tag and is not split into two or more streams.

In accordance with a preferred embodiment of the present invention, the rate of change of the internal wall surface profile is defined by the angle between two lines drawn on any plane constructed alongside the middle of the flow shaping part of the cavity that are tangent to said internal wall surfaces at any two points separated by a distance of 5% of the total length of the cavity where said angle is no greater than 5° excluding the edge of the seat that may form a step not higher than 25% of the tag thickness allowing for fitting tolerance between the tag and the seat.

In accordance with a preferred embodiment of the present invention, the cavity of the capsule contains means of ensuring the tag is inserted in the correct orientation, ensuring the side containing contamination to be removed from, or formed on, is orientated towards the centre of the fluid stream. In accordance with a preferred embodiment of the present invention, the test soil applied to the face surface of the tag comprises between 500 ng and 1 g of protein per every 1 ml of the test soil.

In some embodiments of the present invention, the test soil comprises one or more homogenised animal origin tissues like, but not limited to, brain, liver, kidney, eye, cartilage, blood. Homogenised tissues realistically represent contamination found on medical equipment.

In some embodiments of the present invention, the test soil contains one or more particular proteins like, but not limited to, Hemoglobin, Immunoglobulin G, Transferrin, Aprotinin, Casein, Lactoferrin and/or Insulin. Proteins are used since they are found in most types of tissues and can be accurately detected after the process.

In some embodiments of the present invention, the test soil contains at least one hydrophobic protein like, but not limited to Fibrinogen, Serum Albumin and/or Collagen. Hydrophobic proteins adhere to surfaces very strongly and are much more difficult to remove than hydrophilic ones. Presence of hydrophobic proteins makes contamination removal challenges much more difficult.

In some embodiments of the present invention, the test soil contains a specific quantity of particular proteins such that the evaluation of test result will measure quantities of particular, test specific proteins.

In some embodiments of the present invention means of ensuring the tag is inserted in correct orientation come in the form of but not limited to a one or more cut outs in the internal cavity that fit with the matching keys or tabs.

In some embodiments of the present invention, the capsule contains two or more matching detachable parts that once assembled create the internal cavity. At least one of said parts must be detached to insert a tag inside the cavity and reassembled for the cavity to form the desired sealed shape.

In some embodiments of the present invention, the capsule contains multiple cavities where more than one tag can be inserted where said cavities are arranged in series and or in parallel.

In some embodiments of the present invention, the capsule's inlet is connected to the one or more inlet channels, and the outlet is connected to one or more outlet channels such that the capsule is located in between two or more channels.

The invention provides a method for evaluation of contamination forming and removal processes inside the present invention that simulate the particular size of a hollow channel that can be used to evaluate manual, semi-automatic and automated contamination removal and contamination forming processes for internal surfaces of hollow channels. Said method comprises the insertion of one or more tags into one or more capsules. The tag can be made of different materials metals like, but not limited to, surgical grade stainless steel, titanium or aluminium as well as polymers like but not limited to polytetrafluoroethylene, polyoxymethylene, nylon having its face surface blank or contaminated with a test soil. The face surface of the tag where contamination is applied to and where contamination is formed on has a specific surface finish like, but not limited to surface roughness, nano-structure or nanotexturing, chemical or electrochemical etching or polishing designed to best suit the case. The surface finish affects the test soil adhesion as well as contamination formation on the said surface.

Inside the capsule, the tag is oriented such that its contaminated surface is orientated towards the inside of the cavity. Once the tag is in place, secure it with a lock or a cap. Fully assembled PCD with the tag inside is connected to a source of fluid where the source may be in the form of, but not limited to, fluid container, fluid recirculating rig, sink or bath, ultrasonic bath or washer or washer-disinfector where the capsule is connected directly or through an inlet channel to a fluid source connection port. Executing a contamination forming or removal process under evaluation and thereafter evaluating the face of each tag for remaining contamination either inside the capsule or after removing it from said capsule.

In some embodiments, the method is used for evaluation of contamination removal within which the internal cavity and a tag with test soil are flushed with a cleaning fluid under pressure. The cleaning fluid is, but not limited to, water and/or, liquid cleaning detergents and solvents. Fluid flows from a connection port in the fluid source through the capsule's cavity, simulating conditions in channels of equivalent cross section areas. Inside the cavity, fluid flows through the flow shaping part where the fluid gradually changes shape from the inlet cross-section shape to the cross-section shape of tag holding part of the cavity. In the tag holding part of the cavity where it flows over the face of the tag contaminated with the test soil where the flowing fluid gradually removes the test soil from the face of the tag. Further, fluid flows out through the outlet or through the outlet channel out of the PCD. This embodiment of the method simulates contamination removal from hollow channels of medical or laboratory equipment. After the process, the tag is investigated for any remaining contamination without the need for destructive disassembly of the PCD, with use of available chemical or visual contamination detection techniques.

In a preferred embodiment of the method after depositing the test soil on the surface of the tag, the test soil undergoes a thermal conditioning process having a specific thermal profile. The thermal conditioning process after deposition on the tags is characterised by a thermal profile containing resting at a temperature between 5° C. and 30° C. for 10 min to 10 hours and/or conditioning at temperatures between 25° C. to 150° C. for a period between 1 min and 48 hours. Within the conditioning period, temperature may remain at a constant level or fluctuate within the boundaries.

In some embodiments, the method is used for evaluation of contamination formation on the removable tags simulating microbial growth like in the case of biofilm or chemical or mineral deposits on the internal walls of narrow, hollow channels. The method comprises placing one or more blank samples with appropriately prepared face surfaces that are, but without limitation, cleaned, disinfected or sterilised, primed with surface conditioner, into the one or more capsules, such that each face surface prepared for contamination formation is orientated towards the inside of the cavity. Lock the tag in the capsule with the lock or a cap. Once PCD is assembled, supplying fluid, containing biological contamination and/or mineral and/or metallic residue, through an inlet channel connected to the capsule's inlet, or directly into the capsule's inlet, where it flows through the cavity and tag's face surface is exposed to said fluid in similar manner as the insides of the hollow channels it simulates. After a predefined amount of time, the fluid supply stops and PCD is drained from the fluid, and the tag is evaluated for the presence and character of contamination. Thereafter each capsule can be decontaminated, reassembled, reloaded with another blank tag and reused for another process.

The method allows for removable tags being placed inside the cavity simulating conditions in channels of equivalent cross section areas. This method significantly reduces the difficulty of desorption of biofilm from narrow channels without the need for irreversible destruction of the sample in the testing process. Capsule accepts tags of different materials and surface characteristics, provided they are of a compatible shape to the capsule's cavity, allowing for repetition of the processes conditions and more standardised results.

The present invention provides a PCD for evaluation of cleaning processes of medical and laboratory instruments and equipment and contamination formation on surfaces of various materials and surface characteristics.

An advantage of the present invention is the internal geometry of the cavity containing a seat for holding the tag and which ensures the correct orientation of the tag inside the cavity, creates equivalent flow conditions above the face surface of the tag to the inside of the channel it simulates because of the cross-section area equivalence, resulting in fluid velocity inside of the cavity with the inserted tag being within 90% and 110% of the velocity inside of the channel it simulates.

Another advantage of the present invention are the means for positioning of the tag inside of the cavity in a form but not limited to a tab or key that ensure the tag is inserted in correct orientation with face surface facing the inside of the cavity, allowing for the fluid to always flow against the face surface of the tag such that said tag becomes the fluid stream boundary similar to the wall of the channel it simulates.

Another advantage of the present invention is the flow shaping part of the capsule that does not change the fluid velocity but gradually changes the shape of the fluid stream along the direction of the flow that when said fluid enters the cavity part above the tag no disturbance or sudden change of fluid direction occurs directly above the surface of the tag. The gradual change of the shape of the internal geometry does not disturb the fluid and does not introduce turbulence resulting from the rapid change of the cavity shape.

Another advantage of the present invention is the ability to connect the capsule to channels of equivalent internal cross-section area of different lengths, such that contamination removal or growth are evaluated taking into account resistance to the fluid flow in different channels of a different length.

Another advantage of the present invention is the ability to use smaller orifice outlet in the cap of the capsule in comparison to the capsule inlet to simulate contamination formation or removal in partially blocked channels.

Another advantage of the present invention is the plurality of materials and surface finishes of tags.

Another advantage of the present invention is the compatibility with both biological and chemical test soils, especially those comprise of animal tissue or specific proteins.

Another advantage of the present invention is the capsule's ability to hold the tag in place by means permanently attached to the main capsule body like but not limited to a latch or lock.

A still further advantage of the present invention is the ability to simulate both ends of line setup, where the capsule is placed at the end of the inlet tube; and in line setup, where the capsule is placed between inlet and outlet tube.

A still further advantage of the present invention is the ability to use multiple capsules connected in series or parallel, such that multiple samples are used simultaneously.

A still further advantage is the PCD's compatibility with various contamination detection methods including, but not limited to, visual, chemical and microbiological.

A still further advantage of the present invention is compatibility with the wide range of narrow channels with internal cross-section areas from 0.1 $mm^2$ to 400 $mm^2$ These and other advantages will become apparent from the following description of the present invention and its variants, taken together with the accompanying drawings and the appended claims.

BRIEF DESCRIPTION OF THE DRAWINGS

The present invention may take physical form in certain parts and arrangement of parts, preferred embodiments of which will be described in detail in the specification and illustrated in the accompanying drawings which form a part hereof, and wherein.

DETAILED DESCRIPTION OF THE PRESENT INVENTION

Figure 1:
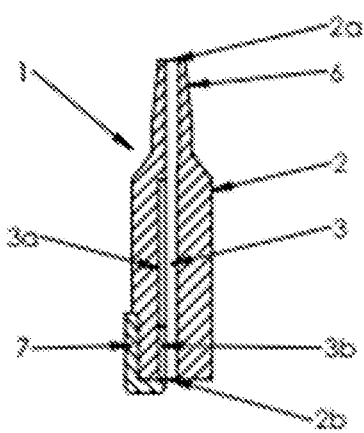
FIG. 1 shows a direct connection embodiment of the PCD.
Figure 2:
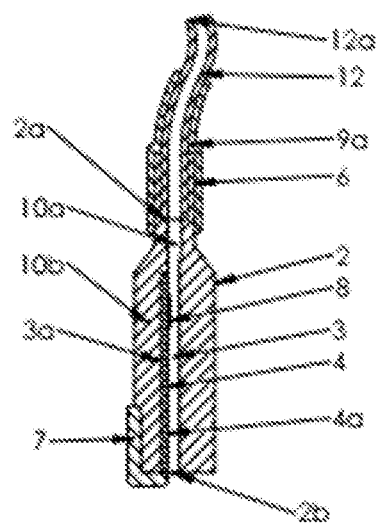
FIG. 2 shows an end-of-line embodiment of the PCD.
Figure 3:
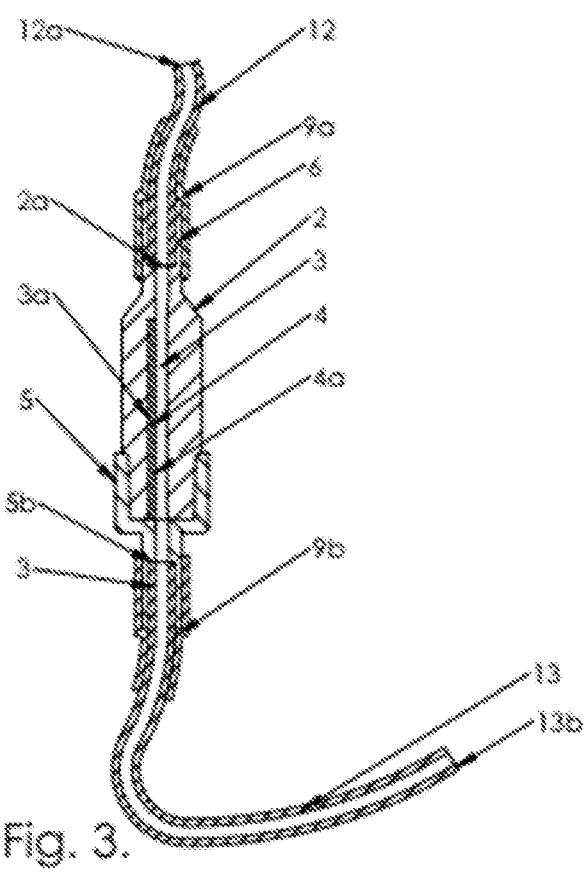
FIG. 3 shows an in-line embodiment of the PCD.
Figure 4:
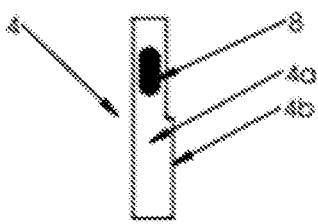
FIG. 4 shows an embodiment of a tag with applied contamination.

Drawings illustrate preferred embodiments of the invention only and are not for the purpose of limiting same. FIG. 1 schematically illustrates a PCD 1 comprised of capsule 2 with an internal cavity 3 having a flow shaping part 10a, a tag holding part 10b, a seat 3a that is a matching shape to the tag into which tag 4 is inserted having a recess 3b for accommodation of a matching tab 4b, inlet connector 6, movable lock 7 for holding the tag 4 in the cavity 3 and a capsule outlet 2b. FIG. 2 schematically illustrates the end-of-line embodiment of the PCD 1 comprised of the inlet tube 12, optionally sleeve 9a and capsule 2 having a lock 7 holding a tag 4 in cavity 3. FIG. 3 schematically illustrates PCD 1 in the in-line embodiment comprised of inlet tube 12, capsule 2, capsule end cap 5 that holds the tag 4 in the cavity 3, outlet connector 6b, and an outlet tube 13 and optionally sleeve 9a and 9b for reinforcement of the bond between the inlet 12 and capsule 2 and or end cap 5 and outlet tube 13. Said inlet and outlet tubes 12 and 13 are attached or not limited to, bonded or inserted into the inlet 2a and outlet of the end cap 5b such that sealed connection is created. FIG. 4 illustrates an example of a non-symmetrical tag 4 with tags top surface known as face surface 4a prepared with a specific surface finish and contaminated with test soil 8.

Referring to the basic operation of the PCD 1, the internal cavity 3 having a seat 3a is formed such that fluid flowing from the cavity inlet 2a, through the flow shaping part 10a into the tag holding part of the cavity 3 does not significantly change the velocity nor the direction of the flow when the tag 4 is positioned inside and the change of fluid stream shape is gradual without edges more than 5° angle. The back surface of the tag 4 is being positioned against the seat 3a such that the face surface 4a of the tag 4 becomes a wall against which the fluid flows. Internal cavity 3 may contain a feature like, but not limited to, a recess 3b that allows insertion of tag 4 having a tab 4b, or another feature, that ensures the tag is positioned in the capsule such that face surface 4a is facing the inside of the cavity and bottom surface fits against the matching shape of the seat 3a. Such geometry of the cavity 3 simulates the fluid flow against the wall or walls of a channel of an equivalent internal cross-section area such that part of wall surface of said channel is represented by the face 4a of the tag 4.

To insert or replace the tag 4 in the capsule 2 the end cap 5 is detached or lock 7 released. Tag 4 is inserted or replaced in the cavity 3 and fits the shape of the seat 3a such that face 4a is orientated towards the inside of the said cavity. Tab 4b and a matching recess 3b are a way of example, but not limitation, of means for positioning of the tag 4 inside the capsule 2 that prevents the insertion of the tag 4 wrong way round. Since the cavity size is relatively small and once inserted only a small proportion of the tag would be visible means of preventing the tag wrong way round are critical. The correct position of the tag in the capsule is essential for its proper functionality. Once tag 4 is in position lock 7 is engaged, or end cap 5 is reattached.

Test soil 8 contains between 500 ng and 1 g of protein for every 1 ml of test soil deposited on the face surface 4a. Test soil may be formed of homogenized tissues containing proteins or specific proteins to achieve particular test soil properties like but not limited to strong adhesion to different types of surfaces, colour or catalysing reactions. In case PCD 1 is used for evaluation of contamination removal, tag 4 containing test soil 8, applied to face surface 4a, is inserted into the cavity 3. PCD 1 is placed in an automated or semi-automated contamination removal equipment or a container dedicated to manual contamination removal. PCD 1 is connected to the source of the cleaning fluid through the inlet tube 12 or directly through a capsule's inlet connector 6. The cleaning process is executed during which fluid flowing through the capsule gradually removes the test soil 8 from the face 4a After the cleaning process tag 4 is evaluated for the presence of remaining contamination inside or after removal outside the capsule 2. Evaluation of remaining contamination may include direct methods evaluating the quantity of contamination directly on the tag's face 4a like in case, but not limited to, visual, fluorescence microscopy or laser spectroscopy as well as indirect methods where remaining contamination is desorbed or eluted and evaluated independently from the tag 4.

When using PCD 1 for evaluation of contamination formation on the tag's 4 face 4a, fluid is supplied into the cavity 3 through the inlet tube 12 in the end-of-line and in-line variants or directly into the capsule 3 through inlet connector 6 such that it flows through the cavity 3 eluting the sample's face 4a. Face 4a is exposed to fluid, allowing for contamination to form on tag's face 4a. After the process, contamination can be evaluated directly on the tag 4 in the capsule 2 or after removal, with, but not limited to, microscopy, fluorescent microscopy or electron scanning microscopy, as well as microbiological and chemical methods. Present invention provides a method of evaluation of contamination removal and formation on the internal walls of channels between 0.1 $mm^2$ and 400 $mm^2$ internal cross-section area where the PCD 1 simulates said channels, the method comprising: providing one or more PCD in any one of embodiments described on FIGS. 1 to 3, wherein the cavity 3 of every capsule 2 contains a tag 4 such that it is secured in position by the lock 7 or end cap 5, connecting PCD 1 to the source of fluid, in series or parallel.

For contamination formation, each tag 4 is decontaminated, disinfected or sterilised with face surface 4a being blank or primed with surface adhesion modifying reagent. Each cavity 3 is supplied with a contaminated fluid containing biological and/or mineral and/or metallic residues diluted or suspended in a said fluid where the flowing fluid has a specific velocity and temperature profile over time. The fluid velocity is between 0m/s and 800 m/s and can be steady throughout the test or fluctuate within the boundaries. Temperature is held at a fixed level for the duration of test or fluctuates between 5° C. and 150° C. Time will vary between 1 minute and 12 weeks depending on the character and thickness of contamination to be formed. The process of contamination forming is followed by evaluating face surfaces 4a of tags 4 while inside capsules or removing them from each capsule by releasing the lock 7 or removing the end cap 5 and evaluating them externally. For contamination removal, each tag 4 contains a test soil 8 applied to the face surface of said tag 4. Each PCD 1 is placed in a container for manual cleaning or inside semi-automatic or automated contamination removing apparatus. Each PCD 1 is connected in series or in parallel to the source of contamination removing fluid, like but not limited to, solvent or detergent. The fluid flows through the capsule and over the face surface 4a of the tag 4 and gradually removes the test soil 8. Fluid is supplied having a specific temperature and velocity profile where the fluid temperature varies between 5° C. and 99° C. and velocity between 0m/s and 800 m/s where both temperature and velocity change over the time. After the process supply of the fluid stops and each face surface 4a is evaluated for remaining contamination while inside capsule 2 or after removing each tag 4 from each capsule 2

EXAMPLES

Example 1

Evaluation of contamination removal effectiveness of 2 mm internal diameter 400 mm long rigid stainless steel endoscope channel in an automated surgical instruments washer for cannulated instruments.

The face 4a of a single-use tag 4 measuring 30 mm in length, 5 mm in width and 0.5 mm thick having an 8 mm long and 1 mm wide tab on the right-hand side of the face, made of mirror polished surgical stainless 316L is inoculated with 5 µl of Test soil 8 containing 10 mg of Bovine Serum Albumin and 1 mg Bovine Collagen per 1 ml of test soil. After inoculation, the test soil is rested for 2 hours at a temperature of 30° C. and an additional 4 hours at 55° C. The end-of-line embodiment of the PCD having a rigid inlet tube of 2 mm internal diameter attached to the inlet connector 6 of the capsule 2 having an internal cavity formed such that seat 3a has a matching shape to the tag 4 and an 8 mm long recess 3b on the right hand side of the surface 3b accommodating the tab of the tag 4 such that once inserted into the cavity 3 tag's face 4a orientated towards the inside of the cavity and cannot be fully inserted other way around. The capsule contains a lock 7 that holds the tag securely in place inside the cavity 3. Cavity 3 above the tag has a cross-section area of 3.14 mm$^2$ equivalent to 2 mm internal diameter of the simulated channel and is shaped such that fluid flows over the entire face of the tag 4. The total length of the PCD including inlet tube, capsule inlet and cavity length is 400 mm simulating the length of the rigid endoscope.

PCD is placed in the chamber of the cannulated instrument washer and connected to the dedicated flushing port for cannulated instruments supplying fluid under pressure. PCD undergoes an automated contamination removal process consisting of 5 min initial rinse with water at 20° C., 20 min main wash with water at 45° C. containing cleaning detergent at a concentration of 5% and a 5 min final rinse with water at 20° C. During each stage, fluid is pumped through the PCD as it would through a surgical instrument it simulates. After the process, PCD is disconnected from the flushing port and removed from the washer. Capsule lock 7 is released, tag 4 is removed and its face 4a evaluated for the presence of remaining contamination by staining the face with a protein stain and examining said surface under a fluorescent microscope. After examination tag 4 is disposed and PCD is appropriately decontaminated and prepared for the next test.

Example 2

Evaluation of biofilm growth in a 1 mm internal diameter 1500 mm long flexible polytetrafluoroethylene (PTFE) tube as used in flexible endoscopes.

Face 4a of a single-use tag 4 measuring 30 mm in length, 5 mm in width and 0.5 mm thick having an 8 mm long and 1 mm wide tab on the right-hand side of the face, made of polytetrafluoroethylene having face 4a having a surface roughness of Ra 6.3 and treated with hydrogen plasma. The in-line embodiment of the PCD having a flexible inlet tube of 1 mm internal diameter attached to the inlet connector 6 of the capsule 2 having an internal cavity formed such that surface 3a has a matching shape to the tag 4 and an 8 mm long recess 3b on the right-hand side of the seat 3a accommodating the tab 4b of the tag 4 such that once inserted into the cavity 3 tags face 4a faces the inside of the cavity and cannot be fully inserted other way around. The capsule contains an end cap 5 that holds the tag securely in place inside the cavity 3 and an outlet tube of the same diameter as the inlet tube. Cavity 3 above the tag has a cross-section area of 0.79 mm$^2$ equivalent to 1 mm internal diameter of the simulated lumen and is shaped such that fluid flows over the entire face of the tag 4. The total length of the PCD including inlet tube, capsule inlet, and cavity length, end cap, end cap outlet and outlet tube is 1500 mm simulating the length of the flexible endoscope.

PCD is placed in a container and connected to the dedicated fluid supply pump. The container holding 1 litre of sterile water at a temperature maintained at 37° C.±0.5° C. and addition of Tryptone Broth growth growing medium at 1% concentration, hereafter known us growing fluid, is supplying a pump delivering a flow rate of 100 ml/min. Said pump's outlet is connected to the inlet tube of the PCD. The outlet tube of the PCD connects back to the container such that fluid circulates from the container, pump, PCD back to the container.

At the start of the process growing fluid is inoculated with 10 ml of *Escherichia coli* at $DO_{600}$ of 2. Growing fluid at a constant temperature circulates between the container and the PCD for 48 hours after which the process ends.

PCD's end cap 5 is removed from the capsule 2, and tag 4 is removed, so the architecture of the biofilms formed on the face 4a is examined under a scanning electron microscope (SEM). After examination tag 4 is disposed and PCD is appropriately decontaminated and prepared for the next test.

Example 3

Evaluation of surgical 316L stainless steel discolouration 4 mm internal diameter channel under a continuous flow of water with a concentration of $SiO_2$ of 100 mg/litre.

Three single-use asymmetric tags 4 measuring 30 mm in length, 5 mm in width and 0.5 mm thick having an 8 mm long and 1 mm wide tab on the right-hand side of the face, is made out of 316L stainless steel with a brushed finish (1200 grit) on face 4a.

The direct connection embodiment of the PCD having the capsule 2 with an internal cavity 3 formed such that seat 3a has a matching shape to the tag 4 and an 8 mm long recess 3b on the right-hand side of the surface 3b accommodating the tab of the tag 4 such that once inserted into the cavity 3 tags face 4a orientated towards the inside of the cavity and cannot be fully inserted other way round. The capsule contains a lock 7 that holds the tag 4 securely in place inside the cavity 3. Cavity 3 above the tag has a cross-section area of 12.57 mm$^2$ equivalent to 4 mm internal diameter of the simulated channel and is shaped such that fluid flows over the entire face of the tag 4. The total length of the PCD including capsule inlet and cavity length is 50 mm.

Three PCDs are loaded with one tag 4 each and connected to the dedicated manifold that is supplied by a pump with a flow of 200 litres a minute. The container holds 10 litres of water at a temperature maintained at 21° C.±0.5° C. and containing $SiO_2$ at a concentration of 100 mg/litre. Said pump's outlet is connected to the manifold through a 20 mm internal diameter, 1000 mm long flexible tube. The outlet of each capsule is directed towards the container such that while the pump is running fluid circulates from the container, through said pump and PCDs back to the container.

Water at constant temperature circulates between the container and the PCD for 72 hours after which pump is topped and PCD's locks are released and tags 4 removed. The faces 4a of the tags 4 are evaluated for $SiO_2$ presence and character visually and with scanning electron microscopy with energy dispersive X-ray spectroscopy.

The above disclosed embodiment(s) is only a preferred embodiment of the present invention and does not intend to limit the scope of the present invention. Any use of equivalent structure or equivalent process alteration made according to the content of these instructions and drawings or any direct or indirect application thereof in other related technical field are equally included in the protection scope of the present invention.

The invention claimed is:

1. A process challenge device (1) comprising:
    at least one removable test tag (4) having a back and a face surface (4a) on which contamination forms or is applied to in a form a test soil (8);
    at least one hollow capsule (2) having an inlet (2a);
    at least one continuous internal cavity (3) inside of the at least one hollow capsule (2), containing:
    a flow shaping portion (10a),
    at least one removable test tag holding part (10b), and
    an outlet (2b), and
    a lock (7) or an end cap (5) for locking the at least one removable test tag (4) in the at least one continuous internal cavity (3) characterised by the at least one removable test tag holding part (10b) of the at least one continuous internal cavity (3) containing:
    a seat (3a) of a matching shape to the at least one removable test tag (4) within which the at least one removable test tag (4) is positioned and an empty space above the seat (3a) wherein said empty space has a cross section area parallel to the cross section of the inlet (2a) and is between 95% and 105% of its size, ensuring the at least one removable test tag (4) is inserted into the seat (3a) in the correct orientation such that the back of the at least one removable test tag (4) sits against the seat (3a) and the face surface (4a) of the at least one removable test tag (4) is orientated towards the space inside of the at least one continuous internal cavity (3);
    the flow shaping portion (10a) of the at least one continuous internal cavity (3) being 1% to 80% of the length of the at least one hollow capsule (2) and providing smooth transition between the cross section shape at the inlet (2a) to the cross section shape of the at least one removable test tag holding part (10b) of the at least one continuous internal cavity (3) at a front edge of the seat (3a).

2. The process challenge device (1) according to claim 1, wherein the smooth transition between the cross-section shape at the inlet (2a) to the cross-section shape of the at least one removable test tag holding part (10b) of the at least one continuous internal cavity (3) at the front edge of the seat (3a) is characterised by the angle between two lines drawn on any plane constructed alongside the middle of the flow shaping portion (10a) of the at least one continuous internal cavity (3), the flow shaping portion (10a), that are tangent to internal wall surfaces at any two points separated by a distance of 5% of the total length of the at least one continuous internal cavity (3) where said angle is no greater than 5°.

3. The process challenge device (1) according to claim 2, wherein a means for ensuring the at least one removable test tag (4) is inserted in the correct position are, but not limited to, in a form of a recess (3b) that fits with the matching feature on the at least one removable test tag (4) like, but not limited to, a key or a tab (4b).

4. The process challenge device (1) according to claim 3, wherein fluid flowing through the at least one continuous internal cavity (3) does not change direction by more than a 5° angle from the direction at the inlet (2a) to the at least one continuous internal cavity (3).

5. The process challenge device (1) claim 4, characterised by the at least one removable test tag (4) is positioned in the seat (3a) such that the at least one removable test tag holding part (10b) of the at least one continuous internal cavity (3) is not fully or partially divided by the at least one removable test tag (4) so that fluid flowing through the at least one removable test tag holding part of the at least one continuous internal cavity (3) flows over the face surface (4a) of the at least one removable test tag (4) is not split into two or more streams by either the at least one removable test tag (4) or the internal geometry of the at least one continuous internal cavity (3).

6. The process challenge device (1) according to claim 5, characterised by the at least one removable test tag (4) is held in the seat (3a) by a lock (7) that needs to be released for the at least one removable test tag (4) to be inserted or removed from the at least one removable test tag holding part (10b) of the at least one continuous internal cavity or the cap (5) that create a continuous sealed cavity between the inlet (2a) of the at least one hollow capsule (2) and an outlet (5b) of the end cap (5) where a seal is in the form of a matching angle tapers (5c) being between of 1° and 200 with 2° tolerance.

7. The process challenge device (1) according to claim 6, wherein the at least one hollow capsule (2) contains a single inlet and is characterised by a plurality of cavities (3) each containing a flow shaping portion (10a) and at least one removable test tag holding part (10b), connected in series or in parallel such that multiple removable test tags (4) can be used simultaneously.

8. The process challenge device (1) according claim 6, where the test soil (8) applied to the face surface (4*a*) comprises one or more specific homogenized tissue of animal origin and Phosphate Buffered Saline (PBS) at a concentration of between 0.5 ml to 50 ml of Phosphate buffered saline per 1 g of tissue.

9. The process challenge device (1) according to claim 6 where the test soil (8) applied to the face surface (4*a*) comprises animal blood and animal homogenised brain tissue mixed at a ratio between 1:1 and 1:10 blood to homogenate.

10. The process challenge device (1) according to claim 6, characterised by the test soil (8) applied to the face surface (4*a*) of the at least one removable test tag (4) contains between 500 ng to 1 g of one or more particular proteins per every 1 ml of where at least one has hydrophobic properties.

11. The process challenge device (1) according to claim 6, wherein the at least one hollow capsule (2) is connected to a hollow inlet channel (12) and/or the end cap (5) is connected to a hollow outlet channel (13) characterised by said hollow inlet channel (12) and the at least one continuous internal cavity (3) form a sealed fluid path of a length between 5 cm and 4 m and/or the hollow outlet channel (13) and, the end cap (5) and the at least one continuous internal cavity (3) form a sealed fluid path of a length between 5 cm and 4 m where the at least one hollow capsule (2) and the end cap (5) sit at the beginning of the sealed fluid path before the hollow outlet channel (13), in-line between the hollow inlet and outlet channels (12) and (13) or at the end of the sealed fluid path and create a continuous fluid line from an inlet (12*a*) or the inlet (2*a*) to an outlet (13*b*) or the outlet (5*b*).

12. The process challenge device (1) according to claim 11, wherein the size of the cross section of any channel (12, 13) connected to the inlet (2*a*) or the outlet (5*b*) of the end cap (5) is between 95% and 105% of the size of the internal cross-section area of the at least one removable test tag holding part (10*b*) of the at least one continuous internal cavity (3) taken across the at least one hollow capsule (2) excluding the cross section area of the at least one removable test tag (4).

* * * * *